(12) United States Patent
Tate et al.

(10) Patent No.: US 6,172,277 B1
(45) Date of Patent: Jan. 9, 2001

(54) NON-TRANSGENIC RODENT MODEL OF ALZHEIMER'S DISEASE

(75) Inventors: Barbara A. Tate, Sharon, MA (US); Ronald Majocha, deceased, late of Sharon, MA (US), by Barbara A. Tate executrix; Julie L. Newton, Pawtucket, RI (US)

(73) Assignee: The Miriam Hospital, Providence, RI (US)

( * ) Notice: Under 35 U.S.C. 154(b), the term of this patent shall be extended for 0 days.

(21) Appl. No.: 08/959,148

(22) Filed: Oct. 28, 1997

(51) Int. Cl.$^7$ .......................... A01K 67/00; A61K 49/00; C12N 15/00; G01N 33/00
(52) U.S. Cl. .................... 800/12; 800/3; 800/21; 800/18; 424/9.2
(58) Field of Search .................. 800/3, 8, 9, 12, 800/14, 18, 21; 424/9.2

(56) References Cited

PUBLICATIONS

Podlisny et al (1992) Neurobiology of Aging 13, 561–567.*
Games et al (1992) Neurobiology of Aging 13, 569–576.*
Frautschy et al (1996) Neurobiology of Aging 17, 311–321.*
Terry et al (1981) Ann. Neurol. 10, 184–192.*
Moran et al (1995) Proced. Natl. Acad. Sci. 92, 5341–5345.*
Hsiao et al (1996) Nature 274, 99–102.*
Frautschy et al., "Rodent Models of Alzheimer's Disease: Rat Aβ Infusion Approaches to Amyloid Deposits", *Neurbiol. Aging* 17:311–321 (1996).
Giordano et al., "Similarities Between β Amyloid Peptides 1–40 and 40–1: Effects on Aggregation, Toxicity In Vitro, and Injection in Young and Aged Rats", *Exper. Neurol.*, 125:175–182 (1994).
Glenner et al., "Alzheimer's Disease: Initial Report of the Purification and Characterization of a Novel Cerebrovascular Amyloid Protein", *Biochem. Biophys. Commun.*, 120:885–890 (1984).
Hayward et al., "Aggregation State of Alzheimer's Amyloid Beta–Protein Determines Behavioral Abnormalities in an Animal Model", *Soc. Neurosci. abs.*, 23(1–2):1638 (1997).

Kang et al., "The Precursor of Alzhimer's Disease Amyloid A4 Protein Resembles a Cell–Surface Receptor", *Nature*, 325:733–736 (1987).
Snow et al., "An Important Role of Heparan Sulfate Proteoglycan (Perlecan) in a Model System for the Deposition and Persistence of Fibrillar Aβ–Amyloid in Rat Brain", *Neuron*, 12:219–234 (1994).
Tate et al., "Chronic Intraventricular Amyloid Infusion: A Paradigm for Induction of Amyloid Accumulations in the Rat Brain", *Soc. Neurosci. abs.* 669.15 (1993).
Tate et al., "Evaluation of Spatial Learning in Rats Receiving β/Amyloid Infusion", *Soc. Neurosci. abs.*, 508.7, (1994).
Tate et al., "Indomethacin Reverses β–Amyloid Induced Gliosis", *Soc. Neurosci. abs.*, 577.17 (1995).
Tate et al., "Beta–Amylid Disturbs Temperature, Activity and Sleep in an Animal Model of Alzheimer's Disease", *Soc. Neurosci. abs.*, 23(1–2) 442.4:1115, (1997).
Tate et al., "Microglial Response to Alzheimer β–Amyloid Protein", *Soc. Neurosci. abs.*, 22(1–3) 81.10:193 (1996).
Yamada, K. et al. l Changes in Ciliary Neurotrophic Factor Content in the Rat Brain after Continuous Intracerebroventricular Infusion of β–Amyloid (1–40) Protein, Neuroscience Letters. 1995, vol. 201, pp. 155–158, especially pp. 156–157.
Itoh, A. et al. Dysfunction of Cholinergic and Dopaminergic Neuronal Systems in β–Amyloid Protein–Infused Rats *Journal of Neurochemistry*. 1996, vol. 66, No. 3, pp. 1113–1117, especially 1114–1116.
Selkoe, D. J. In the Beginning. Nature. Dec. 12, 1991, vol. 354, 432–433, see p. 432, Column 1, paragraph 3.

* cited by examiner

*Primary Examiner*—Deborah Crouch
(74) *Attorney, Agent, or Firm*—Mintz, Levin, Cohn, Ferris, Glovsky and Popeo, P.C.

(57) ABSTRACT

The invention features a method of inducing amyloid plaque deposition in a mammal by infusing into the brain of the mammal an amyloid peptide at a basic pH, a nontransgenic animal model for Alzheimer's disease, and methods of identifying compounds to treat Alzheimer's disease.

32 Claims, 5 Drawing Sheets

NON-TRANSGENIC RODENT MODEL OF ALZHEIMER'S DISEASE

BACKGROUND OF THE INVENTION

The invention relates to neurodegenerative disease.

The role of the β-amyloid peptide (Glenner et al., 1984, Biochem. Biophys. Commun. 120:88–890) in the pathogenesis of Alzheimer's disease is highly controversial. The β-amyloid protein is derived from the transmembrane amyloid precursor protein (APP; Kang et al., 1987, Nature 325:733–736). While deposition of β-amyloid is an invariant feature of Alzheimer's disease, research to date has not elucidated the relationship between β-amyloid plaque deposition and the behavioral and neuropathological features that characterize clinically defined Alzheimer's disease. Studies in vitro have demonstrated that the peptide has both neurotoxic and neurotropic activity, including toxicity in primary cultures of human cortical neurons and dissociated neurons from adult mice. The results of studies in vivo have been less clear.

β-amyloid synthetic peptides, in a variety of sequence lengths and in a number of vehicles, have been administered to the brains of both primates and rodents resulting in only minimal specific neurodegeneration. When administrated by acute injection into either rodents or primates, β-amyloid has failed to consistently produce Alzheimer-specific pathological alterations. Damage induced by the delivery system has been extensive, making it difficult to assess whether amyloid caused specific effects.

A chronic infusion paradigm, in which a mixture of β-amyloid and heparan sulfate proteoglycans are infused, has been reported to produce Congo red positive plaques in rats. Although the β-amyloid peptide of Alzheimer's disease has been implicated in the disease process, the mechanism by which amyloid may contribute to neurodegeneration is not understood.

SUMMARY OF THE INVENTION

The invention features a nontransgenic animal model (e.g., a rat model) of human Alzheimer's disease and a method useful for evaluating strategies to prevent or treat the development of the disease. In addition to the use of the model in evaluating the efficacy of candidate compounds or other therapeutic interventions, the etiology of the disease may be determined using the model.

A method of inducing amyloid plaque deposition in a mammal is carried out by infusing into the brain of the mammal an amyloid peptide at a basic pH, e.g., a pH greater than 8.0 such as a pH greater than 9.0 but less than 11. Preferably, the pH is 9.5.

An amyloid peptide is a peptide derived from human amyloid β protein that causes amyloid plaque deposition in mammalian brain tissue. Preferably, the peptide has an amino acid sequence corresponding to the first 40 amino acids of human amyloid β protein, i.e., the amino acid sequence Asp-Ala-Glu-Phe-Arg-His-Asp-Ser-Gly-Tyr-Glu-Val-His-His-Gln-Lys-leu-Val-Phe-Phe-Ala-Glu-Asp-Val-Gly-Ser-Asn-Lys-Gly-Ala-Ile-Ile-Gly-Leu-Met-Val-Gly-Gly-Val-Val (SEQ ID NO:1).

Amyloid peptide is continuously infused into the brain for at least one week, preferably two weeks, more preferably four weeks, and most preferably eight weeks. Peptides may be infused continuously for a year or more with regular changes of the pump as the contents becomes depleted. Preferably, the amyloid peptide is infused at a concentration of at least 1 mg/ml (preferably in the range of about 1–10 mg/ml, more preferably in the range of about 1–5 mg/ml, and most preferably at about 2 mg/ml). The rate of infusion is about 0.5 μl/hour for about 2 weeks. Preferably, the rate is at least 100 mg per week, more preferably the peptide is infused at a rate of about 200 mg per week. Amyloid peptide is administered to an animal e.g., a rat, at a dose within the range of 0.1 mg/kg to 50 mg/kg of body weight. Preferably, the dose is in the range of 1 to 1.5 mg/kg of body weight.

The invention also features a nontransgenic mammalian model for human Alzheimer's disease. Amyloid plaques are induced in the brain tissue of a nontransgenic mammal, e.g., a rodent such as a rat, mouse, hamster, guinea pig, or degu, by infusing into the brain of the mammal an amyloid peptide at a basic pH for an extended period of time, e.g., weeks to months. In animals that are long-lived (e.g., the degu which has an average life span of about 10 years), the amyloid peptide may be infused for a period of months to years to induce or accelerate plaque deposition and/or other Alzheimer's type pathology.

Animals infused with a peptide having the amino acid sequence of SEQ ID NO:1 develop a plurality of amyloid plaques in their brain tissue. Control animals infused with vehicle alone or a non-toxic control peptide, e.g, a peptide which differs from SEQ ID NO:1 by several amino acid substitutions, develop few or no plaques. Preferably, the sequence of the control peptide is Met-His-Phe-Asp-Gly-Val-Glu-Gly-Phe-Gln-Leu-Ala-Ile-Val-Gly-Asn-Ile-Leu-Val-GLy-GLu-Gly-Gly-Ala-Lys-Val-Val-Asp-Ser-Lys-Ala-Tyr-Phe-His-His-Arg-Asp-Val-Ser-Glu (SEQ ID NO:2).

The nontransgenic model is characterized by Alzheimer's associated disrupted sleep and circadian activity patterns compared to a control mammal (receiving vehicle alone or the control peptide). Control mammals typically develop few or no plaques, whereas mammals infused with the amyloid peptide are characterized by at least a 50% increase in the number of amyloid plaques compared to the number in a control mammal. Preferably, the mammal is characterized by at least a 100% increase in the number of amyloid plaques compared to the number in a control mammal. More preferably, the mammal is characterized by at least a 200% or greater increase in the number of amyloid plaques compared to the number in a control mammal.

Also within the invention is an in vivo screening assay to determine whether a compound reduces deposition of amyloid plaques. The screening assay is carried out by (a) providing a first and second nontransgenic mammal, e.g., a rat, each of which is characterized as having amyloid plaques in a brain tissue (the plaques having been induced by infusing into the brain of each mammal an amyloid peptide at a basic pH); (b) contacting the first mammal with a candidate compound; (c) maintaining the second mammal in the absence of the candidate compound; and (d) comparing the degree of amyloid plaque deposition in the brain of the first mammal with the degree of amyloid plaque deposition in the brain of the second mammal. A lesser degree of deposition in the first mammal compared to that in the second mammal is an indication that the candidate compound reduces amyloid plaque deposition associated with Alzheimer's disease pathology. In addition to quantifying plaque deposition, the screening assay may be used to determine whether a compound reduces an Alzheimer's disease-associated disruption in behavioral abnormalities, e.g., sleep and circadian activity disruptions. In the latter case, the last step of the assay requires comparing a sleep and circadian activity pattern of the first mammal with the sleep and circadian activity pattern of the second mammal.

A lesser degree of disruption of a normal or control pattern (e.g., a pattern obtained from an animal infused with vehicle alone or control peptide) in the first mammal compared to that in the second mammal is an indication that the candidate compound reduces Alzheimer's disease-associated disruption in sleep and circadian activity.

The methods of the invention have several advantages over known methods of inducing amyloid plaques to simulate Alzheimer's type pathology, e.g., reduced mechanical tissue damage from administration procedures, reduced neurotoxicity of vehicle, increased solubility of the peptide over long periods of time (e.g., over the weeks required for continuous infusion protocols), and increased delivery (total load and efficiency of transfer from infusion apparatus) of peptide to brain tissue.

In contrast to prior art control peptides, the control peptide described herein produces few or no amyloid plaques. In addition, amyloid deposition in amyloid peptide-infused animals is associated with a pronounced cellular immune response, wherease infusion of identical amounts of control peptide does not elicit a detectable immune response. This immune response is analogous to that observed in brain tissue derived from human Alzheimer's disease patients.

In contrast to transgenic models of Alzheimer's disease which are harbor DNA encoding amyloid peptide (a significant percentage of which fail to express the recombinant peptide), most or all of the animals chronically infused with amyloid peptide according to the invention develop Alzheimer's type pathology such as amyloid plaque deposition. The amyloid-infused animals also display behavioral symptoms such as disruptions in sleep and circadian rhythm patterns not observed in other rodent models.

Other features and advantages of the invention will be apparent from the following description of the preferred embodiments thereof, and from the claims

DESCRIPTION OF THE PREFERRED EMBODIMENTS

The drawings will first be briefly described.
Drawings

FIGS. 1A–1C are graphs showing a consecutive record of activity data (actogram) and periodgrams of rats infused with representative vehicle (glucose, FIG. 1A), random peptide (FIG. 1B) and β-amyloid peptide (FIG. 1C). Activity events are plotted as verticle bars. Each horizontal line is a 24-hr period, with consecutive days arranged vertically; the data are plotted twice for clarity. The time series analysis or periodogram of the data is shown under the activity data.

DEPOSITION OF AMYLOID PEPTIDE INTO RAT BRAINS

Figure 1A:
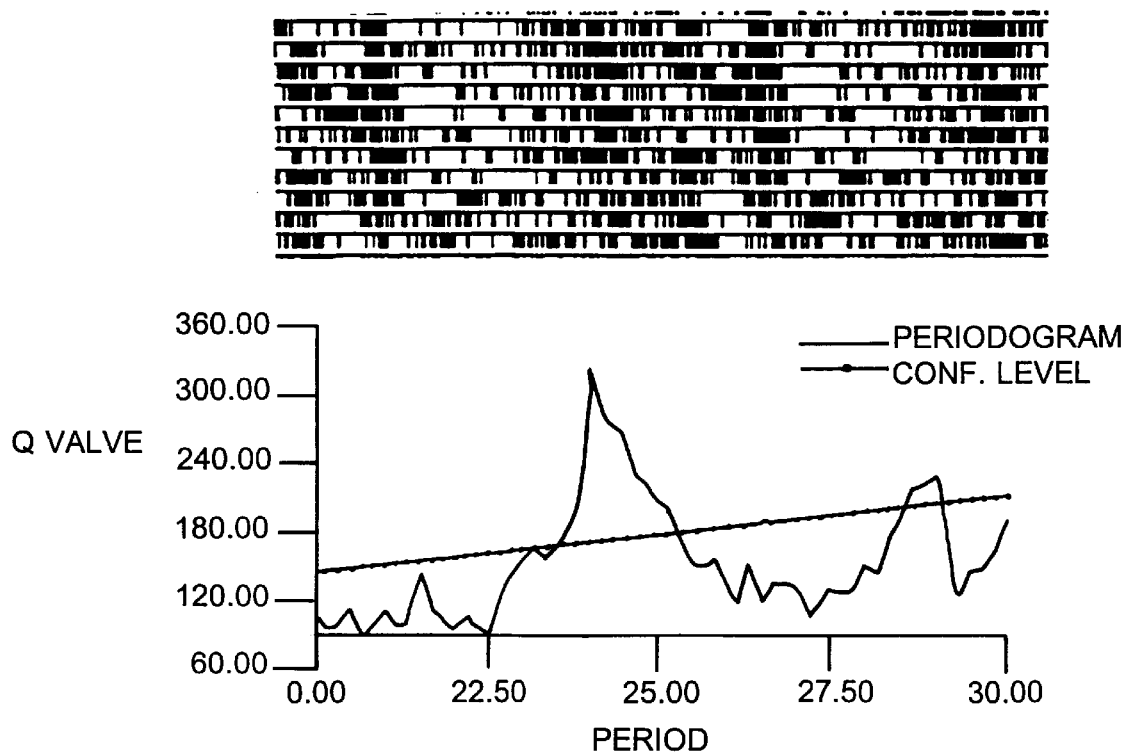

To study the effects of amyloid on brain tissue, a nontransgenic animal model was developed in which amyloid peptide is slowly deposited into the brains of treated animals. Subcutaneously implanted osmotic pumps and in-dwelling intraventricular cannulae were used to chronically infuse synthetic amyloid peptide into rat brains. Amyloid peptide (amino acids 1–40), control peptide or 5% glucose vehicle alone, were infused into the third ventricles of rats over a two week period. Amyloid-infused rats demonstrated disrupted circadian activity rhythms. Deposits of amyloid in periventricular tissue were coincident with marked reactive gliosis, with activated astrocytes and microglia. Similar reactive gliosis was not present in control animals. Chronic intraventricular infusion allowed significant amyloid deposition, which induced disruption of circadian behavior and extensive reactive gliosis. This tissue response has direct relevance to the neurodegenerative changes of Alzheimer's disease.

Alzheimer's disease is characterized by extensive neuronal degeneration. The development of an animal model for human Alzheimer's disease has been complicated by the choice of peptide, vehicle, site and mode of administration and even the use of rodents, which do not naturally develop senile plaques. The vehicle used to administer amyloid peptide in the present model was 5% glucose at basic pH (e.g., pH greater than 9.0, preferably pH 9.5). Amyloid peptide in this vehicle is sufficiently soluble to allow infusion and the vehicle itself does not cause brain tissue damage (as do many other vehicles used to solubilize amyloid peptide). Osmotic pumps were used to microinfuse peptides at a slow rate over an extended period of time (e.g, 1–2 weeks). The cannulae through which the pumps infused amyloid peptide or control substances (i.e., control peptide or vehicle alone) were placed into the third ventricle and not directly into the brain parenchyma. Placement into the brain parenchyma was found to result in a lesion at the tip of the canula, possibly from the pressure with which the pump infuses solution into the brain. Such a lesion may interfere with the interpretation of pathologic tissue reactions to the amyloid infusion. In contrast, cannula placements into the third ventricle resulted in no destruction of the tissue but did result in the presence of significant levels of amyloid peptide in the periventricular tissue as confirmed by immunohistochemical techniques.

EXAMPLE 1

Alzheimer's Disease Associated Immunohistochemical Alterations and Behavioral Abnormalities in a Nontransgenic Animal Model The amyloid peptide administration paradigm described herein allows considerable amyloid load to be applied to the brain in the relative absence of procedure-induced trauma or vehicle-induced tissue damage. The model provides a powerful tool for examining the mechanisms by which the host removes amyloid deposits and recovers from the insult. This model therefore offers unique opportunities to study the effects of amyloid peptide in the mammalian brain in neurodegenerative diseases such as Alzheimer's disease and to screen for therapeutic agents.

Modifications of the standard chronic infusion paradigm were made to maximize the quantity of amyloid delivered while minimizing mechanical damage to the brain. Amyloid peptide was infused into the third ventricle of a rat brain. The periventricular area of the anterior hypothalamus is the anatomical location of major components of the circadian system, including the primary oscillator and the suprachiasmatic nuclei (SCN). Grafts into the SCN of cells transfected with portions of the human β-amyloid precursor protein gene have been shown to induce disrupted activity rhythms. The activity rhythms of amyloid-infused animals were monitored throughout the infusion period and the host tissue response to amyloid deposition was characterized. Extensive reactive gliosis was found to be coincident with areas of amyloid deposition.

Animals

Long-Evans adult male rats were purchased from Charles River Breeding Laboratories (Wilmington, Mass.). Animals were individually housed in standard laboratory cages and provided food and water ad libitum. Four rats received one of each of the following infusions: amyloid 1–40 SEQ ID NO:1; glucose vehicle alone; or control peptide SEQ ID NO:2 which was a scrambled sequence of the amyloid 1–40 mer peptide.

Peptides

Synthetic amyloid peptides corresponding to amino acids 1–40 of the β-amyloid protein and scrambled control β-amyloid peptide were produced synthetically using methods known in the art. The sequences are as follows: β-amyloid—H$_2$N-Asp-Ala-Glu-Phe-Arg-His-Asp-Ser-Gly-Tyr-Glu-Val-His-His-Gln-Lys-leu-Val-Phe-Phe-Ala-Glu-Asp-Val-Gly-Ser-Asn-Lys-Gly-Ala-Ile-Ile-Gly-Leu-Met-Val-Gly-Gly-Val-Val-OH (SEQ ID NO:1); random order (control) peptide—H$_2$N=Met-His-Phe-Asp-Gly-Val-Glu-Gly-Phe-Gln-Leu-Ala-Ile-Val-Gly-Asn-Ile-Leu-Val-Gly-Glu-Gly-Gly-Ala-Lys-Val-Val-Asp-Ser-Lys-Ala-Tyr-Phe-His-His-Arg-Asp-Val-Ser-Glu-OH (SEQ ID NO:2). The peptides were HPLC-purified, dialyzed against 10 μm β-mercaptoethanol to remove contaminants, lyophilized, and shown to aggregate (as evidenced by separation on a 16.5% acrylamide gel). Peptides were dissolved in 5% glucose vehicle, at basic pH (e.g., pH 9.0 or higher (e.g., 9.5) at a concentration of 2 mg/ml.

Since known control peptides (e.g, known random peptides and peptides having an amino acid sequence corresponding to the reverse sequence of residues 1–40 of β/A4 amyloid protein (Giordano et al, 1994, Exper. Neurol. 125:175–182)) have been reported to have biological effects similar to amyloid peptide, a control peptide (SEQ ID NO:2) differing from the active human with several amino acid substitutions from the active human amyloid peptide (SEQ ID NO:1) was produced. These substitutions reduce the hydrophobic nature of the peptide. Molecular modeling predicted a lessening of the degree of folding into a β-pleated sheet conformation. Consistent with the modeling data, the control peptide (SEQ ID NO:2) was found not to stain with Thioflavin S, a dye specific for β-pleated sheet structure.

Antibodies

Two anti-β amyloid antibodies (10H3; 6F/3D, purchased from DAKO) were used. Antibody to glial fibrillary acidic protein (GFAP) was also purchased from DAKO. OX6 (specific for MHC class II antigens) was used to label microglial cells (which express MHC class II antigens when in an activated state).

Surgical Techniques

Stereotaxically-placed infusion cannulae were implanted into the third ventricle just dorsal to optic chiasma (anterior/posterior coordinate relative to Bregma—1.3 mm). The cannulae were 8.5 mm in length. Peptides or vehicle alone (i.e., no peptide) were pumped into the third ventricle by subcutaneously placed mini-osmotic pumps (model 2002, Alza Corp.) that were attached to the cannula by Silastic tubing threaded beneath the skin. The rate of pumping was 0.5 μl/hr for two weeks. Rhythms were continuously monitored in the animals after surgery. Four weeks after pump implantation and two weeks after the pumps had totally discharged their contents, the animals were anesthetized with pentobarbital and euthanized by cardiac perfusion with normal saline followed by 4% paraformaldehyde (PFA) in 20 mM phosphate buffered saline. Assessment of placement and evaluation of immunostaining was done blindly with respect to the evaluation of behavioral outcome of the treatment.

Activity Data Collection and Analysis

Animals were housed under constant dim red light (4 lux) throughout the data collection period. Activity data was collected from each animal via an intraperitoneally implanted radio transmitter (Mini-mitter, Inc., Sunriver, Oreg.) placed in the anesthetized animal at the time of stereotaxic surgery. A radio receiver placed under the cage of each animal accumulated activity data and transmitted it to a computer programmed with a data collection and analysis system (Dataquest III; Datasciences, Inc., Minneapolis, Minn.). The data was stored in 10 minute bins. The mean level of gross motor activity was compared between groups of rats to ensure that amount of gross motor activity was normal prior to evaluation of the pattern or rhythm of activity. Graphic representation of activity data (actograms) was generated for each animal using circadian data analysis software (Cicardia, Behavioral Cybernetics, Cambridge, Mass.).

Statistical Analysis

Activity data was analyzed for the presence of a circadian rhythm by chi square periodogram analysis. Data from a ten day period beginning four days post surgery was analyzed. A 95% confidence level for rhythms with circadian periods were generated and the presence and amplitude of statistically significant rhythms was calculated. Comparisons across groups of mean maximum amplitude within the circadian range was done by analysis of variance (ANOVA) followed by a Tukey's protected t test.

Immunohistology of Brain Tissue Sections

PFA-fixed rat brains were blocked at exactly the same level, anterior to the optic chiasm and posterior to the mamillary bodies, by using a Zivic-Miller rat brain slicer. Tissue was cut on a cryostat at 8 μm and serial sections were collected. Alternate tissue sections were immunostained with hematoxylin-eosin, 10H3 anti-amyloid antibody, 6F/3D anti-amyloid antibody, anti-GFAP and OX6. Anti-GFAP stained sections were counterstained with hematoxylin. Immunostaining was performed using known methods. Briefly, the immunohistochemical procedure was as follows: slide-mounted brain sections were neutralized in 2% H$_2$O$_2$ to block endogenous peroxidase activity. Primary antibodies were appropriately diluted in 10% goat serum, 2% bovine serum albumin (BSA), in a solution of 0.9% NaCl, 20 mM TRIS (pH 7.4), and 0.5% Triton X 100 (TBST). Tissue sections were incubated with primary antibodies overnight at room temperature. Biotinylated secondary antibodies (Jackson Laboratories) were diluted in 2% BSA, TBST at 1 μg/ml. Tissue sections were then incubated in secondary antibody for 2 hours at room temperature followed by incubation in horseradish peroxidase (HRP)-conjugated strepavidin (Sigma) at 0.5 μg/ml in TBST with 2% BSA for 2 hours at room temperature. The chromogen typically used was diaminobenzidine. However, for doubly-labelled tissue, fluorescently tagged secondary antibodies (rhodamine-conjugated goat anti-mouse for 10H3 and fluorescein conjugated goat anti-rabbit for GFAP, Cappel) were used. Sections were incubated in a solution of secondary antibody for 1 hour. Slices were rinsed in TBST three times for 10 minutes, then rinsed in TBS for 5 minutes. A coverslip was applied to the slide using 10% polyvinyl alcohol. As a control, tissue sections were incubated with no primary antibody (all other steps for the procedure were the same). Tissue sections were counterstained with hematoxylin. Immunostained tissues were examined and photographed with a Zeiss MC63 photographic system attached to a Zeiss standard microscope equipped with a mercury lamp and appropriate filters for viewing rhodamine and fluorescein fluorescence.

Behavioral Abnormalities

Figure 1B:
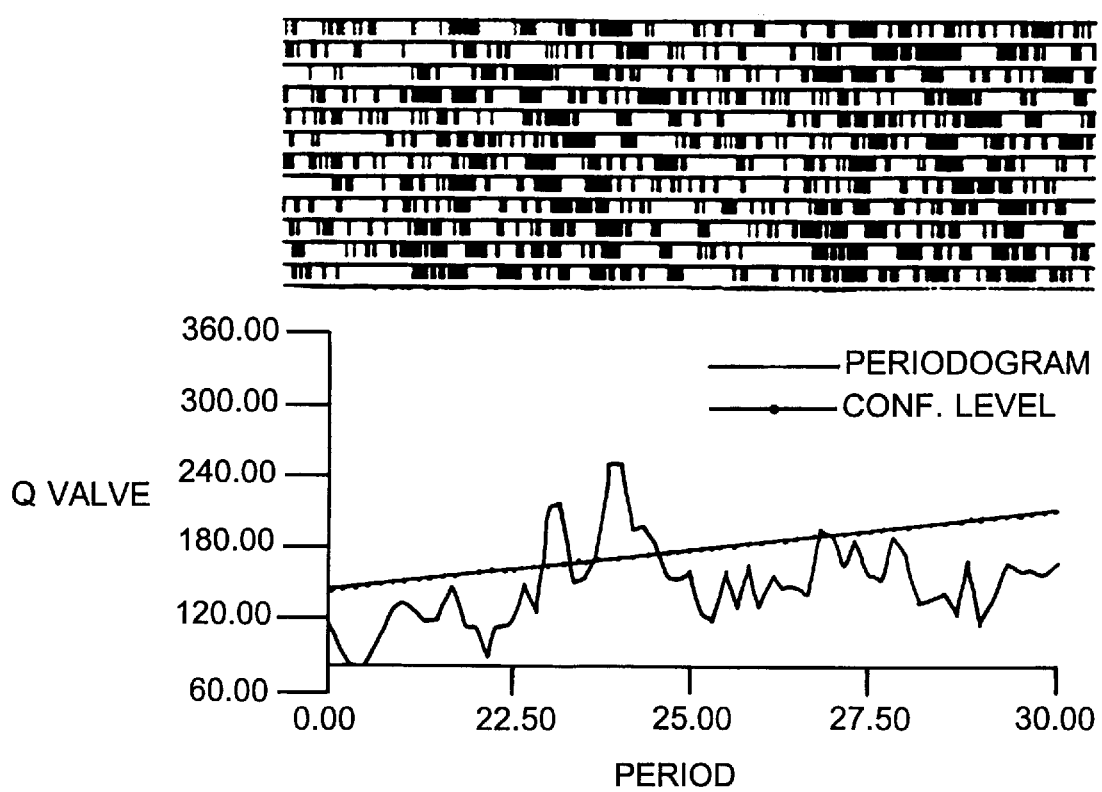
Figure 1C:
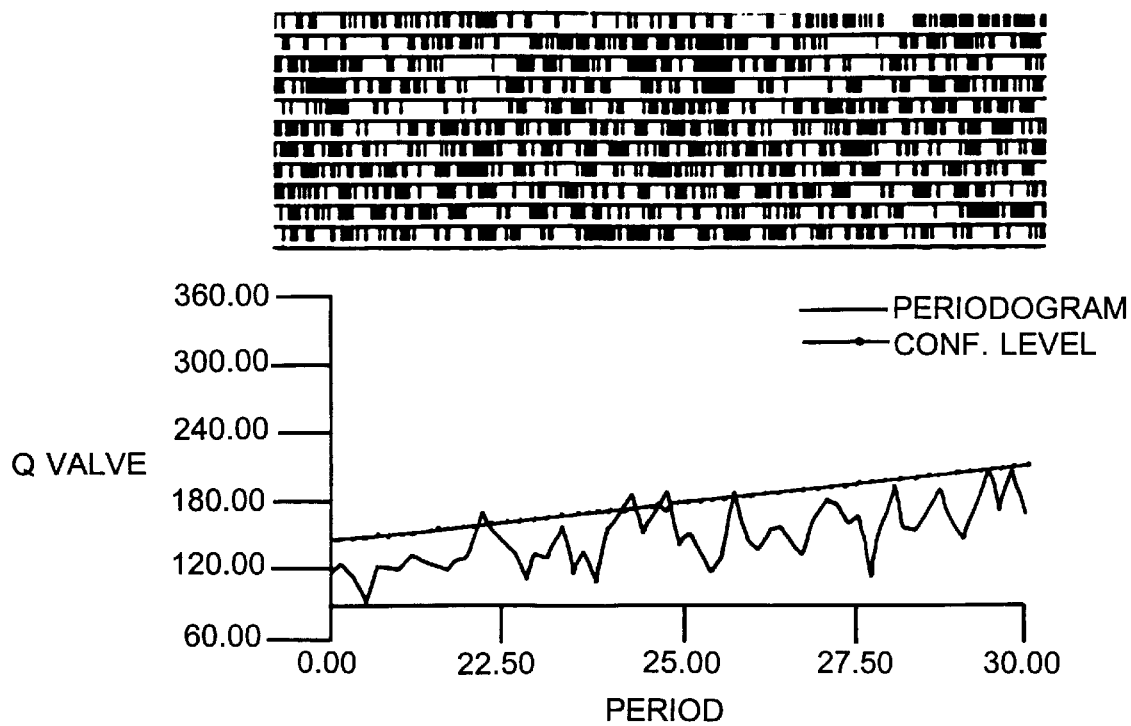

Behavioral data from representative animals are shown in FIGS. 1A–1C. All of the glucose infused animals (FIG. 1A) had normal activity rhythms; significant peaks in the periodogram appear within the circadian range. Under conditions of constant dim red light, rats display free running rhythms, with periods that approximate, but are not exactly, 24 hours. The most significant period in the periodograms of activity rhythms of glucose control rats ranged between 23.83–24.33 hours.

Control peptide-infused animals displayed activity rhythms with significant circadian periods, although two of the four subjects had weaker rhythms, with lower amplitude Q values, than any of the glucose infused animals (FIG. 1B). Irregular onsets in activity were apparent in these animals, as seen in the actogram for the representative control peptide infused animal.

FIG. 1C shows the actogram and the accompanying periodogram for a representative amyloid peptide infused animal. Within the circadian range, only weakly significant periods are presenting the data set. None of the amyloid petide-infused rats had strong peaks within the circadian range in the periodograms of activity data. The amyloid peptide-infused animals also displayed deficits in the water maze test (a test of learning and memory).

Immunohistology

Hematoxylin-eosin stained sections were examined from all animals to confirm cannulae placement sites. In all subjects, cannula tips were place within the third ventricle. Serial 8 $\mu$m tissue sections (taken prior to and throughout the area of the cannula track) were immunostained with two different amyloid-specific antibodies: an antibody which binds to GFAP and an antibody which binds to microglial cells. In amyloid-infused rats, both anti-amyloid antibodies gave similar patterns of staining. Anti-amyloid immunopositive material was distributed along the entire length of the ventricle and extended up to 800 $\mu$m into the periventricular tissue. At higher magnification, the immunopositive material appeared granular, extending in a concentration gradient from the ventricular lining, where it was heavily deposited to hundreds of microns into the periventricular tissue where it ended in a clear demarcation. Some staining was visible in the white matter of the optic chiasma, indicating infusion of amyloid into the white matter.

Adjacent sections from amyloid peptide-infused animals were immunostained with antibodies to GFAP. Reactive astrocytes were visible along the third ventricle and at the top and bottom of the ventricle. In addition, heavy GFAP immunopositive staining was visible in areas of amyloid deposition that were not coincident with mechanical damage. A double labelling procedure demonstrated coincidence of $\beta$-amyloid immunopositive areas and GFAP positive areas.

Animals that received either control peptide or glucose vehicle infusions were also examined. Although the animals receiving control peptide infusion showed uniform immunostaining along the ventricle, the granular deposits seen in the amyloid peptide-infused animals were not visible in either of the control groups. In both control groups, immunostaining appeared to be slightly darker in areas of mechanical damage. No specific immunoreactivity was present with anti-amyloid antibody in animals that had received glucose vehicle only. Sections from animals infused with either control substance (control peptide or vehicle alone) were also immunostained with antibodies to GFAP. Gliosis was present in areas of mechanical damage. However, the extent of gliosis was significantly reduced when compared to amyloid peptide-infused animals. Hypertrophied reactive astrocytes (which were clearly visible in amyloid peptide-infused animals) were not prominent in the control groups.

Reactive microglia and macrophages were detected in amyloid peptide-infused animals. Sections were stained with OX6 antibody (which labels activated microglia and macrophages). Although immunopositive deposits were detected at the surface of the third ventricle in both control peptide and amyloid peptide-infused rats, the extent of staining was significantly greater in the amyloid-infused rats. Animals infused with vehicle alone showed weak immunoreactivity with OX6 antibody and little change of microglia morphology from the nonreactive state.

Alzheimer's Type Pathology in a Nontransgenic Animal Model

Behavioral abnormalities was induced by amyloid infusion. Animals with amyloid deposition into the anterior hypothalamus displayed severe disruption of normally rhythmic activity behavior. Control peptides or glucose vehicle did not induce similar behavioral disruption.

Chronic infusion allowed sufficient accumulation of $\beta$-amyloid peptide into the brain parenchyma with little or no associated tissue damage. The distribution of amyloid in the periventricular tissue was not uniform but suggested that some areas of neuropil adjacent to the ventricle may have allowed greater penetration. Intraventricular infusion as described above permits delivery of amyloid peptide into the neuropil without causing significant mechanical damage. As a result, it is possible to more accurately assess the effects of amyloid peptide on brain tissue.

Gliosis is also described in Alzheimer's disease brain tissue. The appearance of reactive astrocytes and activated microglia at the site of $\beta$-amyloid accumulation occurs during the development of a mature senile plaque in the human brain. Microglia, the endogenous mononuclear phagocyte of the brain, possess complement receptors for Cqlb. When activated, e.g., by infections, foreign substances or degeneration, these cells express MHC class II antigens. When stimulated, microglial cells can therefore be detected by MHC class II antibodies (e.g., OX6).

Activated microglia are present in Alzheimer's disease brain tissue, but whether microglia are activated directly by $\beta$-amyloid or secondarily by neuronal damage is uncertain. Activated microglia and macrophages (as visualized with OX6 antibody) were found to be present in amyloid and control peptide-infused rats. Although the vehicle-infused animals demonstrated some reactivity with the OX6 antibody, the reactive cells maintained a dendritic morphology. The low level of expression of MHC class II antigen in the animals infused with vehicle alone may reflect the macrophage/microglia response to mechanical damage of the infusion procedure. The vehicle-infused animals showed weak staining and the absence of microglia and macrophages with morphological changes associated with activation. Control peptide-infused animals showed some activated cells while $\beta$-amyloid peptide-infused animals showed dense infiltration of activated cells in the areas of peptide deposition.

The presence of a foreign protein such as the control peptide or $\beta$-amyloid peptide appeared to stimulate microglia and macrophages. The number of activated cells were greater in the presence of amyloid peptide than in the presence of the control peptide.

Activated microglia secrete interleukin 1 (IL-1) and interleukin-6 (IL-6). These cytokines can stimulate APP expression, an event that could lead to production of β-amyloid. Additionally, IL-1 has been demonstrated to stimulate astrocytes to secret a1-anti-chymotrypsin, a molecule found to be associated with amyloid plaques. Furthermore, in vitro, a1-antichymotrypsin has been shown to promote the polymerization of amyloid filaments which could enhance amyloid deposition. These data indicate that microglia play an etiological role in the pathogenesis of Alzheimer's disease and may provide a therapeutic target.

Dramatic astrocytic gliosis was visible in areas of amyloid deposition in amyloid peptide-infused rats. This was especially striking when the area of deposition did not coincide with an area of mechanical damage. Extensive reactive gliosis was observed in association with the infused amyloid deposits. In the short time interval between amyloid deposition and euthanasia of the animals, astrocytic responses were well established.

EXAMPLE 2

Vehicle Determination for Amyloid Peptide Administration

In order to deliver amyloid peptide into the rat brain in a chronic infusion paradigm using a mini-osmotic pump, it was necessary to maintain the peptide at a high concentration (2 mg/ml) solution in a bio-comparable vehicle at 37° C. for two to four weeks (or longer). Although salt solutions are bio-compatible, amyloid will precipitate out of a physiological saline solution. It was discovered that 5% glucose was both bio-osmotic and that amyloid would dissolve in this vehicle. However, it was found that amyloid would, over time, precipitate out of solution. The pH of the 5% glucose solution was critical to maintaining amyloid peptide in solution of the time period (weeks) necessary to allow chronic infusion into the rat brain. Experiments were therefore carried out to test which buffers would be best to maintain 5% glucose at an alkaline pH while allowing amyloid peptide to remain in solution for several weeks.

Existing infusion protocols are problematic due to clogging of the infusion apparatus resulting from, e.g, fibril formation in the osmotic pump and precipitation/aggregation in the pump or tubing. To avoid such problems, a vehicle composition was formulated to optimize peptide solubility and effectiveness of delivery. Solubility of the peptide, effectiveness of delivery, and stability was tested at various pHs, e.g., pH 7.4, 8.0, 8.7, 9.0, 9.5, 10.5, and 11 (in various buffer systems, e.g., TRIS, Hepes, Na Phosphate, and Carbonate/Bicarbonate). Generally, the pH had to be raised to a basic pH in order to solubilize the amyloid peptide. The effectiveness of various vehicles in allowing maximal amyloid delivery was carried out by examining the brains of rats after the two week infusion period. The amount of Thioflavin S positive and immunopositive amyloid deposits in the brains of these rats was assessed. Peptide dissolved, remained stable and in solution for the period of time required for delivery (i.e., weeks) in vehicle having a pH greater than 9 and up to a pH of about 11. The vehicle found to be most effective in maintaining amyloid in solution (and amyloid delivery to the brain) was 5% glucose buffered to pH 9.5 in a 0.1 M carbonate/bicarbonate buffer. Since the carbonate/bicarbonate buffer system is relatively weak, the peptides are maintained in solution at basic pH during the infusion process but are converted to a physiological pH soon after entering the body.

EXAMPLE 3

Sleep and Circadian Rhythm Disruption in an Animal Model of Alzheimer's Disease The severe sleep fragmentation seen in Alzheimer's disease is profoundly disruptive on a variety of levels and can contribute to the patients' cognitive problems, including impairments in attention, judgement, decision making, and memory. Irregular and unpredictable sleep is often the event that precipitates institutionalization of the patient. It has been suggested that sleep fragmentation in Alzheimer's disease, characterized by frequent night time awakenings, may reflect disturbances of the circadian system while significant reductions in slow wave sleep (SWS) and rapid eye movement (REM) sleep may result from cytokine dysregulation and cholinergic deficits, respectively.

Using the rat model described herein, deposition of human amyloid protein was shown to induce a pronounced inflammatory response. These animals also show circadian rhythm disruption. To investigate whether these animals also exhibited sleep disturbances, human amyloid peptide was slowly infused for two weeks into the cerebral ventricles of the rats (adult male Long Evans rats). Control animals received either (1) a control amyloid peptide the sequence of which differs from the naturally-occurring sequence by several amino acids substitutions or (2) 5% buffered glucose vehicle alone.

Activity rhythms were monitored throughout the infusion by in-dwelling radio transmitters. Circadian activity rhythms were disrupted in the amyloid-infused rats, but not in rats that received a control peptide or vehicle only. At the end of two weeks, the animals were euthanized and the brains processed for histological and immunohistochemical evaluation. Immunopositive deposits of amyloid were found to surround the ventricles of amyloid infused rats. Fibrillary amyloid was present, as evidenced by Thioflavin S staining and by electron micrographic examination of a subgroup of animals. A pronounced cellular immune response was found in the areas of amyloid deposition, with large numbers of reactive astrocytes and activated microglia surrounding the amyloid deposit. These data suggest that both a cellular immune response and disrupted circadian activity rhythms result from amyloid deposition in the brain.

In the another study, two adult male rats were given both stereotaxic placement of lateral ventricle cannulae and EEG/EMG electrodes. Following a one week recovery period, during which the animals continued to be housed under a 12:12 light-dark schedule. Polysomno-graphic recordings of EEG/EMG were carried out across 24 hours. The animals were then anesthetized and implanted with osmotic pumps containing the 1–40 amyloid beta peptide; the peptide was pumped through the cannula for one week, at which time polysomnographic recording of EEG/EMG were again carried out across 24 hours.

Figure 2:
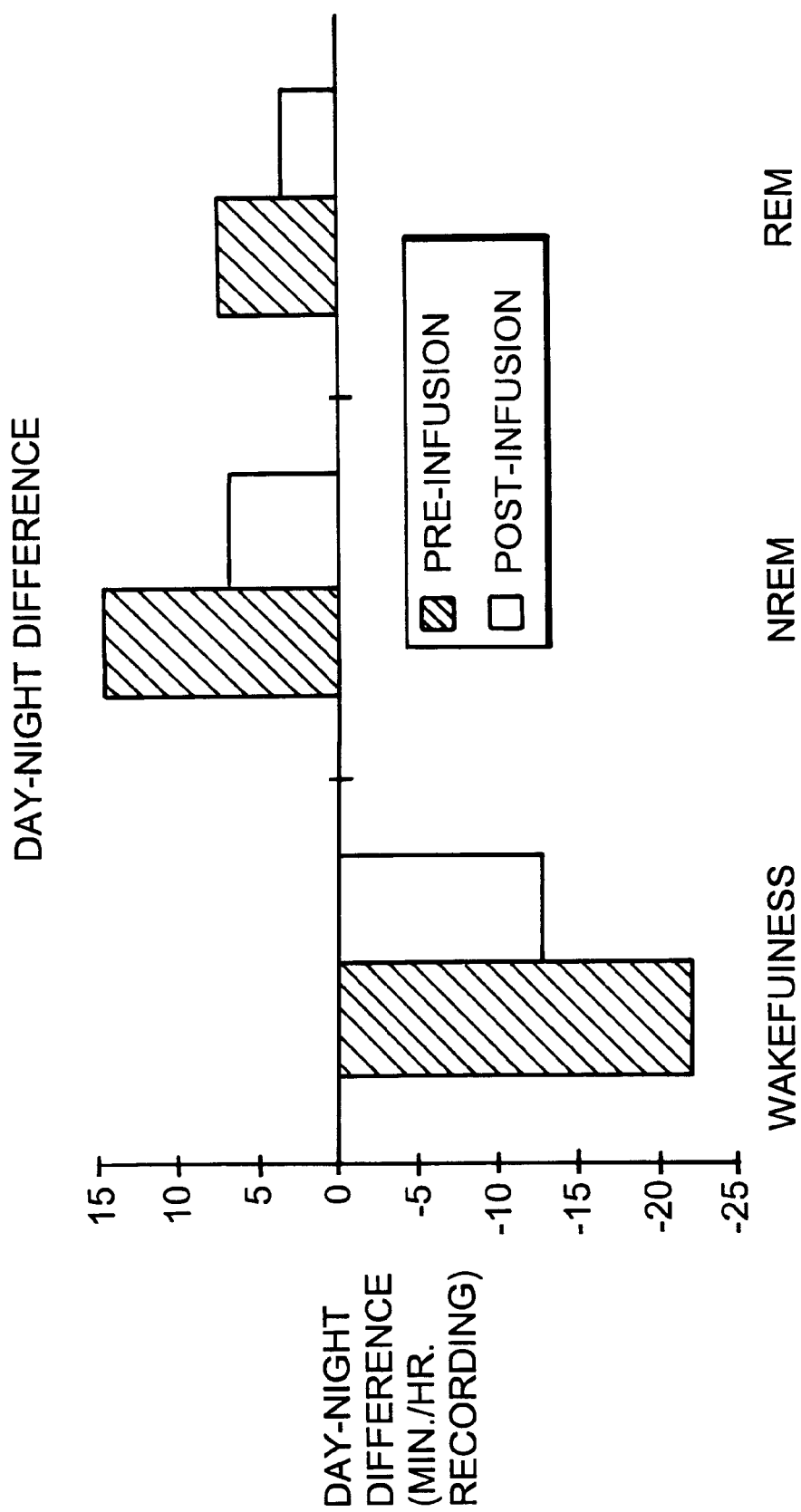
FIG. 2 is a bar graph showing the average day-night differences in wakefulness (non-REM (NREM) and REM sleep) in amyloid-infused rats prior to and after one week of intraventricular infusion of amyloid peptide.
Figure 3:
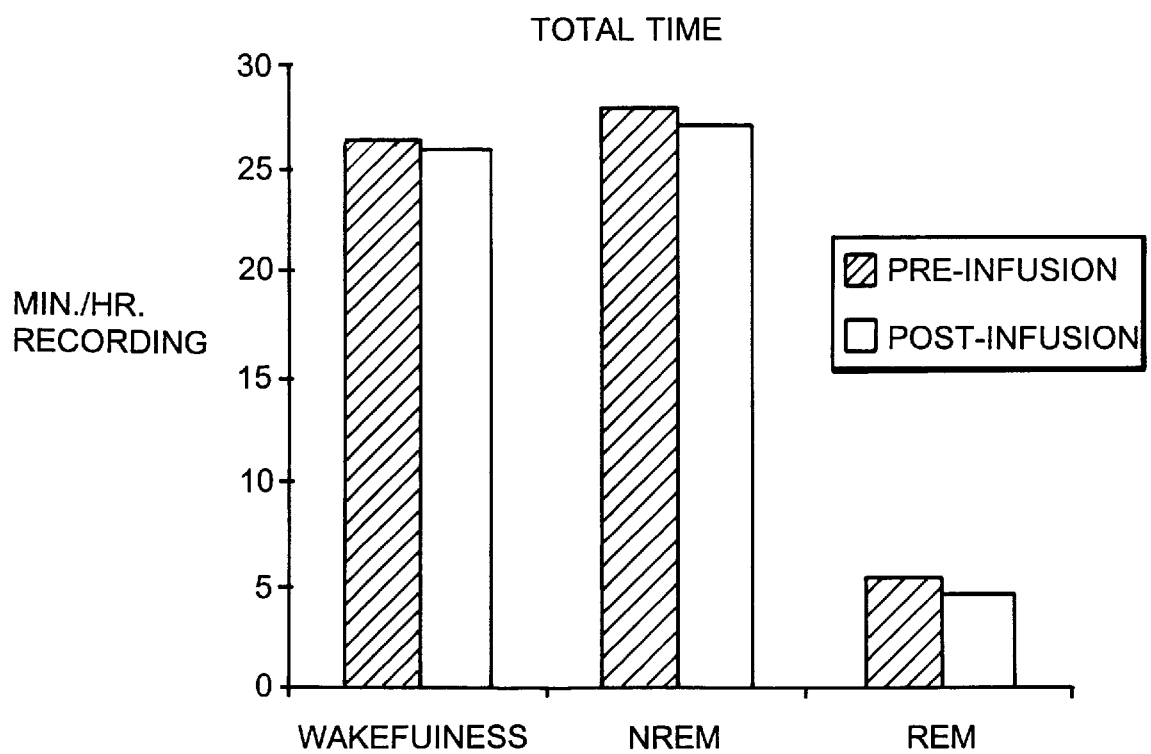
FIG. 3 is a bar graph showing the total amount of wakefulness (NREM and REM sleep) in amyloid-infused rats prior to and after one week of intraventricular infusion of amyloid peptide.

FIG. 2 shows the average day-night differences in wakefulness, non-REM (NREM) and REM sleep prior to (pre-Infusion) and after one week of intraventricular infusion of amyloid (post-infusion). Post-infusion, there is a marked decrease in the day-night differences in all three parameters. However, as shown in FIG. 3, the total amount of wakefulness, NREM and REM sleep did not change pre- and post-infusion.

These data indicate that later ventricle infusion of amyloid disrupts the circadian distribution of sleep and wake, a result consistent with the finding that amyloid infusions in the third ventricle disrupted circadian activity patterns. The alteration in circadian activity and sleep rhythms in the rat following amyloid infusion mimics the alteration seen in human Alzheimer's patients. Thus, the model described herein is useful to uncover the molecular mechanisms that result in sleep disruption in Alzheimer's disease (including the relationship between the pronounced cellular immune response induced by amyloid deposition and circadian and sleep abnormalities) and for screening candidate compounds for the ability to reduce the pathological symptoms of human disease.

EXAMPLE 4

Aggregation State of Alzheimer's Amyloid Beta-protein Determines Behavioral Abnormalities in an Animal Model The aggregation state and neurotoxic potential of the amyloid peptide to infuse rat brains was evaluated using an NT2 cell (American Type Culture Collection (ATCC) No. CRL-1973)-based assay to quantitate toxicity and a thioflavin-S binding assay to measure the formation of β-sheet fibrils. Amyloid peptide was either pre-treated (1 mg/ml in water, dialyzed against β-mercaptoethanol and re-lyophilized) or resuspended directly at 2 mg/ml in 5% glucose, pH 9.5. Pretreated peptide was maximally toxic at 280 nM monomeric peptide equivalents. During a 15 day incubation under the conditions used for pump infusion into animals, peptide toxicity remained unchanged. No toxicity (at a 1000-fold higher concentration) was seen with monomeric amyloid peptide [464 $\mu$M] prepared directly from lyophilized powder in PBS buffer pH 7. This peptide became toxic when allowed to aggregate over 15 days. Incubation of this peptide in 5% glucose, pH 9.5 buffer accelerated the formation of toxic aggregates. Toxic peptide had a four-fold or greater thioflavin-S fluorescence signal compared to freshly prepared monomeric peptide solution.

The third ventricle of Long Evans rats was perfused via a subcutaneous osmotic minipump containing either: preincubated peptide; monomeric peptide or vehicle. Circadian activity was monitored continuously under constant dim red lighting for the next two weeks and analyzed by: (i) chi-square periodogram analysis. A moving average with a twelve hour window was calculated across the data set and the highest and lowest average activity values were calculated and expressed as a consolidation index: (ii) blindly rated on a scale of 1–10 for stability of the circadian activity rhythm. Animals receiving pretreated amyloid infusion had more disrupted circadian cycles compared to vehicle alone or monomeric amyloid treated animals. These data indicate that the amyloid peptide preparations most effective in disrupting circadian rhythm behavior when infused into the ventricle of rats are in an aggregated and highly toxic physical state prior to infusion and that this toxicity is preserved during the infusion period

EXAMPLE 5

Amyloid Peptide Infusion Disturbs Temperature, Activity and Sleep in an Animal Model of Alzheimer's Disease Alzheimer's disease is associated with attenuation of the diurnal rhythms of sleep and wakefulness, manifesting clinically as disturbed sleep and increased napping during the day. To investigate whether the pathophysiology of these sleep-wake disturbances is due to increased cytokine expression reflecting a generalized central nervous system (CNS) inflammatory response, an analogous inflammatory response was produced in the rat by prolonged infusion of human amyloid protein. The infusion results in large numbers of reactive astrocytes and activated microglia surrounding fibrillary (Thioflavin S positive) amyloid deposits, as well as high levels of inducible nitric oxide synthase (iNOS). The immune response is specific, i.e., the control peptide infusion does not elicit a cellular immune response. To examine the effects of amyloid infusion on sleep/wake ventricle cannula, EEG/EMG electrodes and an intraperitoneal transmitter were used to continuously measure activity and temperature of the animals. After a one week recovery period, polysomongraphic (PSG) recordings of EEG/EMG were carried out for 48 hours. The animals were then re-anesthetized and implanted with osmotic pumps containing amyloid β (1–40) or control peptide. After one week of infusion, 48 hour PSG recordings were repeated. Animals were then euthanized and brains prepared for immunohistochemistry. Relative to baseline, treatment PSG data showed reduced amplitude of diurnal rhythms of wakefulness, NREM sleep and REM sleep in amyloid animals. Temperature and activity rhythms were similarly disrupted. In the 24 hours immediately following infusion, an acute rise in body temperature was seen in amyloid animals but not in the animals infused with the control peptide. Temperature returned to baseline and was not elevated during the second sleep recording. Histopathology showed evidence of cellular immune response in amyloid animals but not in controls. Thus, amyloid infusion produces a disruption of the diurnal rhythms in sleep/wake state, motor activity and temperature, coincident with signs of ongoing cellular immunologic activation, but well after an acute febrile response. These results suggest that a pathophysiologic mechanism for the sleep abnormalities of Alzheimer's disease is a generalized CNS inflammatory response characterized by a cellular immune response.

EXAMPLE 6

Screening for Therapeutic Compounds

The nontransgenic animals of the invention can be used to screen candidate compounds or other therapeutic approaches for the ability to reduce amyloid plaque deposition or lessen the behavioral symptoms, e.g, disruption in sleep and circadian rhythms, of Alzheimer's disease. In such an assay, animal in which plaque deposition has been induced by chronic infusion of amyloid peptide at a basic pH are treated, e.g., contacted with a candidate compound, or left untreated, e.g., no compound whatsoever is administered or vehicle alone is administered. The candidate compound may be administered to the animals before, during, or after infusion of the amyloid peptide.

The animals receiving the candidate compound are then compared at various time points for the development of Alzheimer's type pathology to those not receiving the compound. A reduction in Alzheimer's type pathology (measured, e.g., by quantification of plaque deposition, quantification of microglia infiltration and/or activation, detection of cytokine disregulation such as increased IL-1 or IL-6 production in brain tissue, or assessment of sleep and/or circadian rhythm disturbances) compared to untreated animals indicates that the candidate compound is efficacious in the treatment or prevention of Alzheimer's disease.

EXAMPLE 7

Indomethacin Reverses the Microglial Response to Amyloid-β Protein

Alzheimer's disease brains display intense microglial immunoreactivity in the area of senile plaques, suggesting that amyloid β-protein may stimulate microglial infiltration. The activated microglia may modulate an immune response in the brain. Non-steroidal anti-inflammatories (NSAIDs) are candidate therapeutics for Alzheimer's disease because their effects on immune system components may influence the course of the disease. The effects of a non-steroidal anti-inflammatory drug (indomethacin) on amyloid β-protein induced microglial infiltration was examined. Amyloid peptide was chronically infused into rat lateral ventricles for two weeks. Extracellular amyloid β-protein was deposited along the lining and diffused into the tissue surrounding the lateral ventricle in amyloid-peptide infused animals. Immunocytochemical staining showed that animals receiving amyloid peptide exhibited a dramatic microglial response when compared to animals infused with vehicle alone. Active microglia surrounded immunopositive amyloid β-protein deposits, but this response was significantly attenuated in animals receiving either subcutaneous treatment with indomethacin or intraventricular infusion of indomethacin directly into the brain. These results suggest that chronic amyloid peptide infusion induces microglial cell infiltration and proliferation of active microglia. Indomethacin was found to be effective to inhibit microglial proliferation.

Animals

Male Long-Evans rats were purchased from Charles River Breeding Laboratories, Wilmington, Mass. All animals were 8 to 10 weeks of age and weighed 300–400 grams at the time of surgery. The rats were acclimated to laboratory conditions for one week before undergoing surgery. After surgery, rats were individually housed in plastic cased under a 12:12 light-dark schedule (lights on 0700–1900). Food and water were available ad libitum.

Surgical Procedures

Animals were anesthetized with an intramuscular injection of ketamine (55 mg/kg body weight), acepromazine (1 mg/kg body weight), and xylazine (5 mg/kg body weight). A stainless-steel osmotic pump connector cannula (28 gauge; Plastics One, Roanoke, Va.) 4.4 mm in length was implanted into the lateral ventricle using stereotaxic coordinates 1.4 mm posterior and ±2.0 mm lateral relative to Bregma, and was fixed to the skull using stainless steel screws and cranioplastic cement. The animals were allowed to recover for one week, after which they were anesthetized and miniosmotic pump(s) (Model 2002, Alza Corp) were inserted in a subdermal pocket overlying the scapula and connected by Silastic tubing (Dow Corning) to the cannula. Rate of pumping was 0.5 $\mu$l/hour for two weeks. In some cases, rats were infused with peptides for longer periods of time, e.g., 4 weeks or 8 weeks. Animals can be infused with peptides in the vehicle described above for a year or more. Longer infusion times require replacing the osmotic pump infusion apparatus as it becomes depleted.

Prior to implantation, osmotic pumps were primed by pre-incubation in 0.9% saline solution at 37° C. for 2 hours. Pumps contained either amyloid peptide or TRIS buffered 5% glucose vehicle pH 8.7. A total dose of 200 mg of peptide was available for delivery. The peptide forms thioflavin positive β-pleated sheet in vitro and in vivo.

In one experiment, six rats received simultaneous intraventricular infusion of indomethacin salt in water (200 mg total dose) and amyloid peptide. Six control rats received amyloid and the water vehicle only.

In another experiment, ten animals were infused bilaterally with amyloid peptide. Five of the ten animals were randomly selected to receive twice daily subcutaneous injections of indomethacin (1.8 mg/ml in water; 0.5 ml/injection; 1.8 mg/day; 25.2 mg total dose). The other 5 animals received twice daily subcutaneous injections of sterile water.

Sacrifice of Animals

Two weeks after pump implantation, rats were deeply anesthetized with sodium pentobarbital (1 mg/kg) and perfused intracardially 4% paraformaldehyde (PFA). Pumps were removed and analyzed for amount of fluid remaining, protein concentration, and signs of infection. Brains were removed and postfixed in 4% PFA overnight. Brains were cryoprotected in 30% sucrose, and sectioned on a cryostat at 8 $\mu$m onto treated glass microscope slides (Superfrost Plus, Fisher).

Immunostaining

Immunostaining was carried out using standard methods. The primary antibody was either an anti-amyloid monoclonal antibody supernatant (10H3) specific for a 28 amino acid peptide corresponding to the first 28 amino acids of amyloid β-protein or a monoclonal antibody (OX6) specific for MHC class II antigens which are expressed by active microglia. Both antibodies were used at a concentration of 1 $\mu$g/ml. Controls included tissue submitted to all steps of the procedure except for the addition of primary antibody.

Analysis of Brain Tissue Sections

Tissue sections were examined using an image analysis system consisting of a high resolution black and white camera (Javelin, model JE7362), Optimas software (Laser Pix, Woburn, Mass.). Sections were examined for amyloid deposition and microglial response. Cells immunostained with OX6 antibody were examined and quantified. For each subject, the number of immunoreactive cells was counted in six randomly chosen non-overlapping microscopic fields coincident with areas of amyloid deposition. In addition, the total area from which counts were made was measured. The average number of immunopositive cells per unit area was calculated and a mean number of immunopositive cells in the indomethacin-treated group and in the group that received vehicle alone was calculated for each group and compared by student's t-test.

In animals receiving infusions of amyloid peptide, immunopositive amyloid depositions were detected along the lining of, and into the tissue surrounding the lateral ventricle. Activated microglia surrounded immunopositive amyloid β-protein.

To determine whether microglial activation was dependent upon the presence of amyloid or if mechanical damage alone induced a response, animals were infused with vehicle alone (5% buffered glucose). Animals receiving vehicle alone exhibited areas of mechanical damage due to cannula implantation; however, these areas found to be devoid of immunopositive amyloid deposits and activated microglia. In the indomethacin-treated animals, intraventricular infusion of indomethacin completely suppressed the microglial response to amyloid deposits.

Another experiment was undertaken to determine whether indomethacin administered by the more conventional route of subcutaneous injection would also inhibit the microglial response to amyloid β-protein. Pump analysis confirmed successful delivery of amyloid peptide to 3 of 5 animals receiving subcutaneous indomethacin injections, and 5 of 5 animals receiving water injections. In both groups of animals, thioflavin S positive deposits were detected. These deposits were immunopositive amyloid β-protein deposits extending into the ventricular tissue from the site of infusion. Animals receiving water injections (no indomethacin) showed a massive activated microglial response to the amyloid β-protein deposits, whereas animals receiving indomethacin injections showed a marked suppression of this response.

Cell counts of OX6-positive cells in areas of amyloid deposition were compared between the two groups: water vehicle-treated animals and indomethacin-treated animals. Water vehicle treated rats had a mean of 6 immunopositive cells/1000 m area, and indomethacin-treated rats had a mean of 19 immunoreactive cells/1000 um area. These data indicate that deposition of amyloid peptide stimulates microglia activation even when surrounding tissue did not show evidence of degeneration.

Microglia from Alzheimer's disease brains have been reported to have amyloid β-peptide within the cell, but it is controversial as to whether they are a source or whether they have phagocytized amyloid β-protein form the surrounding tissue. The time course of appearance of microglia in Alzheimer lesions, the factors which stimulate activation, and the nature of the role in plaque formation (amyloid production verses amyloid uptake) are critical issues to understanding the pathogenic process of Alzheimer's disease. The data discussed above indicate that indomethacin reduces the microglial response to amyloid peptide infusion and suggest that inhibition of microglia activation (e.g., by administering either locally or systemically a nonsteroidal anti-inflammatory agent such as indomethacin) as a therapeutic approach to treatment of Alzheimer's disease.

2. The method of claim 1, wherein said peptide comprises the amino acid sequence Asp-Ala-Glu-Phe-Arg-His-Asp-Ser-Gly-Tyr-Glu-Val-His-His-Gln-Lys-leu-Val-Phe-Phe-Ala-Glu-Asp-Val-Gly-Ser-Asn-Lys-Gly-Ala-Ile-Ile-Gly-Leu-Met-Val-Gly-Gly-Val-Val (SEQ ID NO:1).

3. The method of claim 1, wherein said pH is greater than 8.0.

4. The method of claim 3, wherein said pH is greater than 9.0.

5. The method of claim 4, wherein said pH is greater than 9.0 but less than 11.

6. The method of claim 5, wherein said pH is 9.5.

7. The method of claim 1, wherein said amyloid peptide is continuously infused into said brain for at least one week.

8. The method of claim 7, wherein said amyloid peptide is continuously infused into said brain for at least two weeks.

9. The method of claim 1, wherein said amyloid peptide is infused at a concentration of at least 2 mg/ml.

10. The method of claim 1, wherein said amyloid peptide is infused at a rate of at least 100 mg per week.

11. The method of claim 1, wherein said amyloid peptide is infused at a rate of about 200 mg per week.

SEQUENCE LISTING

<160> NUMBER OF SEQ ID NOS: 2

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
 1               5                  10                  15

Leu Val Phe Phe Ala Glu Asp Val Gly Ser Asn Lys Gly Ala Ile Ile
                20                  25                  30

Gly Leu Met Val Gly Gly Val Val
            35                  40

<210> SEQ ID NO 2
<211> LENGTH: 40
<212> TYPE: PRT
<213> ORGANISM: Homo sapiens

<400> SEQUENCE: 2

Met His Phe Asp Gly Val Glu Gly Phe Gln Leu Ala Ile Val Gly Asn
 1               5                  10                  15

Ile Leu Val Gly Glu Gly Gly Ala Lys Val Val Asp Ser Lys Ala Tyr
                20                  25                  30

Phe His His Arg Asp Val Ser Glu
            35                  40

Other embodiments are within the following claims.

What is claimed is:

1. A method of inducing amyloid plaque deposition in a rodent, comprising infusing into the brain of said rodent a solution comprising a β-amyloid peptide at a basic pH, wherein the infusion of said peptide results in the formation of amyloid plaques in the brain of said rodent in a greater number than in a control rodent infused with buffer alone or receiving a control peptide.

12. The method of claim 1, wherein said peptide is infused at a rate of about 0.5 µl/hour.

13. A transgenic rodent comprising amyloid plaques in its brain tissue wherein said plaques are induced by infusing into the brain of said rodent a solution comprising a β-amyloid peptide at a basic pH, and wherein said rodent has at least a 50% increase in the number of amyloid plaques compared to the number of plaques in a control rodent infused with buffer alone or receiving a control peptide.

14. The rodent of claim 13, wherein said amyloid peptide is continuously infused into said brain for at least one week.

15. The rodent of claim 13, wherein said amyloid peptide is continuously infused into said brain for at least two weeks.

16. The rodent of claim 13, wherein said amyloid peptide is continuously infused into said brain for at least eight weeks.

17. The rodent of claim 13, wherein said amyloid peptide is continuously infused into said brain for at least one week to one year.

18. The rodent of claim 13, wherein said amyloid peptide comprises the amino acid sequence Asp-Ala-Glu-Phe-Arg-His-Asp-Ser-Gly-Tyr-Glu-Val-His-His-Gln-Lys-leu-Val-Phe-Phe-Ala-Glu-Asp-Val-Gly-Ser-Asn-Lys-Gly-Ala-Ile-Ile-Gly-Leu-Met-Val-Gly-Gly-Val-Val (SEQ ID NO:1).

19. The rodent of claim 13, wherein said pH is greater than 8.0.

20. The rodent of claim 13, wherein said pH is greater than 9.0.

21. The rodent of claim 13, wherein said pH is greater than 9.0 but less than 11.

22. The rodent of claim 13, wherein said pH is 9.5.

23. The rodent of claim 13, wherein said rodent is a rat.

24. The rodent of claim 13, wherein said rodent is a mouse, hamster, guinea pig, or degu.

25. The rodent of claim 13, wherein said rodent has a disrupted sleep and circadian activity compared to the control rodent.

26. The rodent of claim 13, wherein said rodent has at least a 100% increase n the number of amyloid plaques compared to the number in the control rodent.

27. The rodent of claim 13, wherein said rodent has at least a 200% increase in the number of amyloid plaques compared to the number in the control rodent.

28. An in vivo screening assay to determine whether a candidate compound reduces deposition of amyloid plaques, comprising:

(a) providing a first and second nontransgenic rodent, each of which comprises amyloid plaques in a brain tissue, wherein said plaques are induced by infusing into the brain of each rodent an β-amyloid peptide at a basic pH;

(b) contacting said first rodent with said candidate compound;

(c) maintaining said second rodent in the absence of said candidate compound; and (d) comparing the degree of amyloid plaque deposition in the brain of said first rodent with the degree of amyloid plaque deposition in the brain of said second rodent, wherein a lesser degree of deposition in said first rodent compared to that in said second rodent is an indication that said candidate compound reduces amyloid plaque deposition.

29. The assay of claim 28, wherein said first nontrangenic rodent and said second nontransgenic rodent are rats.

30. An in vivo screening assay to determine whether a candidate compound reduces an Alzheimer's disease-associated disruption in sleep and circadian activity, comprising:

(a) providing a first and second nontransgenic rodent, each of which comprises amyloid plaques in a brain tissue, wherein said plaques are induced by infusing into the brain of each rodent an β-amyloid peptide at a basic pH;

(b) contacting said first rodent with said candidate compound;

(c) maintaining said second rodent in the absence of said candidate compound; and (d) comparing a sleep and circadian activity pattern of said first rodent with the sleep and circadian activity pattern of said second mammal, wherein a lesser degree of disruption of said pattern in said first rodent compared to that in said second rodent is an indication that said candidate compound reduces Alzheimer's disease-associated disruption in sleep and circadian activity.

31. The assay of claim 30, wherein said first nontransgenic rodent and said second nontransgenic rodent are rats.

32. A polypeptide comprising the amino acid sequence of Met-His-Phe-Asp-Gly-Val-Glu-Gly-Phe-Gln-Leu-Ala-Ile-Val-Gly-Asn-Ile-Leu-Val-GLy-GLu-Gly-Gly-Ala-Lys-Val-Val-Asp-Ser-Lys-Ala-Tyr-Phe-His-His-Arg-Asp-Val-Ser-Glu (SEQ ID NO:2).

* * * * *

UNITED STATES PATENT AND TRADEMARK OFFICE
CERTIFICATE OF CORRECTION

PATENT NO. : 6,172,277 B1
DATED : January 9, 2001
INVENTOR(S) : Barbara A. Tate, Ronald Majocha and Julie L. Newton It is certified that error appears in the above-identified patent and that said Letters Patent is hereby corrected as shown below:

Claim 13, column 2,
Line 60, after "A", delete "transgenic", and insert -- nontransgenic --.

Signed and Sealed this

Twenty-fifth Day of September, 2001

Attest:

NICHOLAS P. GODICI
Attesting Officer
Acting Director of the United States Patent and Trademark Office